United States Patent
Bischoff et al.

(10) Patent No.: US 8,262,223 B2
(45) Date of Patent: Sep. 11, 2012

(54) DEVICES AND METHODS FOR DEFINED ORIENTATION OF AN EYE

(75) Inventors: Mark Bischoff, Bad Berka (DE); Marco Hanft, Jena (DE); Elke Ebert, Jena (DE); Gregor Stobrawa, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 886 days.

(21) Appl. No.: 12/224,960

(22) PCT Filed: Mar. 8, 2007

(86) PCT No.: PCT/EP2007/001984
§ 371 (c)(1),
(2), (4) Date: Sep. 10, 2008

(87) PCT Pub. No.: WO2007/104460
PCT Pub. Date: Sep. 20, 2007

(65) Prior Publication Data
US 2009/0073382 A1 Mar. 19, 2009

(30) Foreign Application Priority Data
Mar. 10, 2006 (DE) .................. 10 2006 011 624

(51) Int. Cl.
*A61B 3/10* (2006.01)
*A61B 3/00* (2006.01)
(52) U.S. Cl. .................. 351/211; 351/200; 351/221
(58) Field of Classification Search .............. 351/200, 351/205, 206, 211, 220, 221
See application file for complete search history.

(56) References Cited

U.S. PATENT DOCUMENTS

| 4,762,410 | A | * | 8/1988 | Sekiguchi et al. ............ 351/206 |
| 6,145,990 | A | | 11/2000 | Uchida |
| 6,830,336 | B2 | | 12/2004 | Fransen |
| 6,968,127 | B2 | | 11/2005 | Nanjyo |
| 2002/0047991 | A1 | * | 4/2002 | Jaggi ............................. 351/209 |
| 2002/0102099 | A1 | | 8/2002 | Saito |
| 2005/0286019 | A1 | | 12/2005 | Wiltberger et al. |

FOREIGN PATENT DOCUMENTS

| DE | 41 08 435 | 10/1991 |
| DE | 198 12 050 | 9/1999 |
| DE | 100 16 839 | 6/2001 |
| DE | 101 51 314 | 4/2003 |

(Continued)

*Primary Examiner* — Thomas K Pham
*Assistant Examiner* — Brandi Thomas
(74) *Attorney, Agent, or Firm* — Frommer Lawrence & Haug LLP

(57) ABSTRACT

The present solution is directed to the orientation of an eye for diagnostic and/or therapeutic purposes, wherein the line of sight need not coincide with the optical axis of the examination apparatus or treatment apparatus. The invention includes a fixating light source for generating a positionable fixating mark, a device for coupling this fixating mark into a beam path of an ophthalmological apparatus whose imaging optics project the fixating mark on the eye to be examined and/or treated, and a control unit by which the image of the fixating mark can be displayed at different distances and angular positions with respect to the optical axis of the ophthalmological apparatus so that the eye to be examined and/or treated is oriented to this fixating mark by foveal focusing and occupies a defined position with respect to the optical axis of the ophthalmological apparatus.

8 Claims, 2 Drawing Sheets

FOREIGN PATENT DOCUMENTS

| | | |
|---|---|---|
| DE | 103 14 944 | 10/2004 |
| DE | 102 54 369 | 11/2004 |
| DE | 103 59 239 | 7/2005 |
| EP | 1 452 126 | 9/2004 |
| WO | 02/053020 | 7/2002 |
| WO | 03/057023 | 7/2003 |

* cited by examiner ated unit for ophthalmological devices for illuminating/irradiating the human eye for purposes of observation and/or treatment. The light generated by the illumination source is coupled into the observation system by devices for generating special illumination patterns such as, e.g., filters, diaphragms and/or optoelectronic light modulators and optical means such as beamsplitters, semitransparent mirrors, or the like. The illumination patterns generated in this way are projected into the patient's eye by projection optics and the objective of the ophthalmological apparatus.

DEVICES AND METHODS FOR DEFINED ORIENTATION OF AN EYE

The present application claims priority from PCT Patent Application No. PCT/EP2007/001984 filed on Mar. 8, 2007, which claims priority from German Patent Application No. 20 2006 011 624.1 filed on Mar. 10, 2006, the disclosure of which is incorporated herein by reference in its entirety.

BACKGROUND OF THE INVENTION

1. Field of the Invention

The present invention is directed to a device and a corresponding method for the defined orientation of an eye for diagnostic or therapeutic purposes, wherein the line of sight need not necessarily coincide with the optical axis of the examination apparatus or treatment apparatus.

2. Description of Related Art

In ophthalmology, it is known in diagnostic or therapeutic methods to position and orient the patient's eye with a certain accuracy in relation to a device suitable for carrying out the method. The orientation and positioning of the eye in question is generally carried out on or along the optical axis of the apparatus in question.

For this purpose, the patient's head was fixed by means of a chin support and/or forehead support and the apparatus was then positioned by the operator in such a way that the patient's eye was situated so as to be approximately centered in front of the optical system of the apparatus. If the patient was lying down on a couch, for example, the couch was generally moved with the patient and oriented to the optical system of the apparatus. In every case, the detection and evaluation of the position of the eye of the patient is first carried out by the operator in that the patient's eye is observed directly via an optical or electronic observation system and is positioned corresponding to the apparatus such as an ophthalmological examination instrument or a surgical microscope.

After positioning, the orientation of the patient's eye, i.e., the orientation of its line of sight, is usually carried out by showing the patient a fixating light to which the eye is oriented. The fixating light supplied by the device is usually generated by a separate light source and is blended into the optical axis of the device so that the eye of the patient is oriented along the optical axis of the device and the fixating light is focused on the macula of the patient. According to the known prior art, continuously illuminating fixating marks as well as blinking fixating marks are used for this purpose.

In therapeutic ophthalmological devices in particular, the orientation of the patient's eye is acquired and evaluated so that any faulty orientation can be taken into account in the therapeutic treatment. In this automatic position acquisition, known as tracking, neither the patient's eye nor the fixating light is moved.

DE 102 54 369 A1 describes an ophthalmological apparatus with an eyetracker unit for measuring structures by means of variably structured illumination patterns by which eye movements can be compensated by tracking. For this purpose, the illumination pattern is moved relative to the apparatus corresponding to a detected eye movement, i.e., the illumination pattern is tracked by the eye movement and thus appears to be "connected" to the eye. The eyetracker unit which is used for detecting the eye movement is coupled with the optical axis of the observation system and delivers signals which exactly define the pupil center.

The illumination pattern is preferably generated by IR illumination so that it is only visible to the operator and not to the patient and is evaluated by a corresponding camera.

DE 103 14 944 A1 describes an illuminating and irradiating unit for ophthalmological devices for illuminating/irradiating the human eye for purposes of observation and/or treatment. The light generated by the illumination source is coupled into the observation system by devices for generating special illumination patterns such as, e.g., filters, diaphragms and/or optoelectronic light modulators and optical means such as beamsplitters, semitransparent mirrors, or the like. The illumination patterns generated in this way are projected into the patient's eye by projection optics and the objective of the ophthalmological apparatus.

Although this solution serves primarily to illuminate an eye, generated illumination patterns can be tracked by means of an eyetracker unit relative to the apparatus corresponding to a detected eye movement.

In this solution, the illumination pattern is also only visible to the operator and not to the patient and the detected eye movement is tracked.

By means of the method described in DE 103 59 239 A1 for displaying a fixating mark for ophthalmological treatment devices, unwanted eye movements of an eye to be treated are prevented or at least minimized. For this purpose, the fixating mark is projected in the field of view of the patient so that the patient orients the eye to be treated on the fixating mark by foveal focusing. In a particular construction, the fixating mark is moved in such a way that the patient can follow the movement.

However, the fixating mark can also be used for specific positioning of the eye, wherein the fixating mark is projected in the visual field of the eye to be treated so that the patient orients the eye to be treated on the fixating mark through foveal focusing. The fixating mark is then moved in such a way that the patient can follow the movement.

In contrast to the references mentioned thus far, DE 41 08 435 describes an arrangement for monitoring fixation which can preferably likewise be applied for devices for examination of the visual field, but principally also for other ophthalmological examination instruments. For this purpose, means are provided for rotating a structured fixating mark around a central axis to furnish a functional, reproducible fixation stimulus. The fixating mark has a structure and a predominant direction which can only be identified by the test subject when foveally fixated by the test subject. This is achieved in that the fixation mark is formed, for example, as a Landolt ring which adopts discrete directional orientations when rotated. A Geneva drive generates the discrete directional orientations of the fixating mark from a uniform rotating movement in 90-degree rotations with a stationary period. The test subject must constantly follow the slit of the Landolt ring during the examination, which can be accomplished only with corresponding foveal fixation.

Although the fixating mark is visible to the patient in this solution, the fixating mark cannot be used for specifically positioning the eye because, except during a brief stationary phase, the fixating mark is moved constantly and the line of sight of the eye being examined or treated accordingly changes. Further, this solution only affords the possibility for the fixating mark to appear with a certain variation (rotation) only in a predetermined direction.

SUMMARY OF THE INVENTION

It is the object of the present invention to develop a solution by which an eye to be examined and/or treated can be oriented so as to occupy a defined position with respect to the optical axis of the ophthalmological apparatus.

According to the invention, this object is met by the features of the independent claims. Preferred further developments and constructions are the subject matter of the dependent claims.

The solution according to the invention for the orientation of an eye for diagnostic and/or therapeutic purposes comprises a fixating light source for generating a positionable fixating mark, a device for coupling this fixating mark into a beam path of an ophthalmological apparatus whose imaging optics project the fixating mark into the eye to be examined and/or treated. The image of the fixating mark can be displayed at different distances and angular positions with respect to the optical axis of the ophthalmological apparatus so that the eye to be examined and/or treated is oriented to this fixating mark by foveal focusing and occupies a defined position with respect to the optical axis of the ophthalmological apparatus.

The proposed technical solution is applicable in principle in all ophthalmological devices used for diagnostic and/or therapeutic purposes. However, orientation in a defined position with respect to the optical axis of the ophthalmological apparatus is important particularly for the observation and/or treatment of the anterior segments of the eye.

In the solution for the orientation of an eye for diagnostic and/or therapeutic purposes, a visible fixating mark is presented to the patient's eye and the patient orients his/her eye on this fixating mark by foveal focusing. For a new orientation, the fixating mark is displaced in a corresponding manner. The reference to the optical axis of the ophthalmological apparatus is always taken into account.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The device according to the invention for the orientation of an eye for diagnostic and/or therapeutic purposes comprises a fixating light source for generating a positionable fixating mark and a device for coupling this fixating mark into a beam path of an ophthalmological apparatus whose imaging optics project the fixating mark onto the eye to be examined and/or treated, and a control unit by which the image of the fixating mark can be displayed at different distances and angular positions with respect to the optical axis of the ophthalmological apparatus so that the eye to be examined and/or treated is oriented to this fixating mark by foveal focusing and occupies a defined position with respect to the optical axis of the ophthalmological apparatus.

In a first embodiment form, the fixating light source for generating the positionable fixating mark comprises a separate light source with at least one scanning mirror arranged in front of it. A self-luminous object or its image or an illuminated diaphragm or its image is used as the separate light source.

Figure 1:
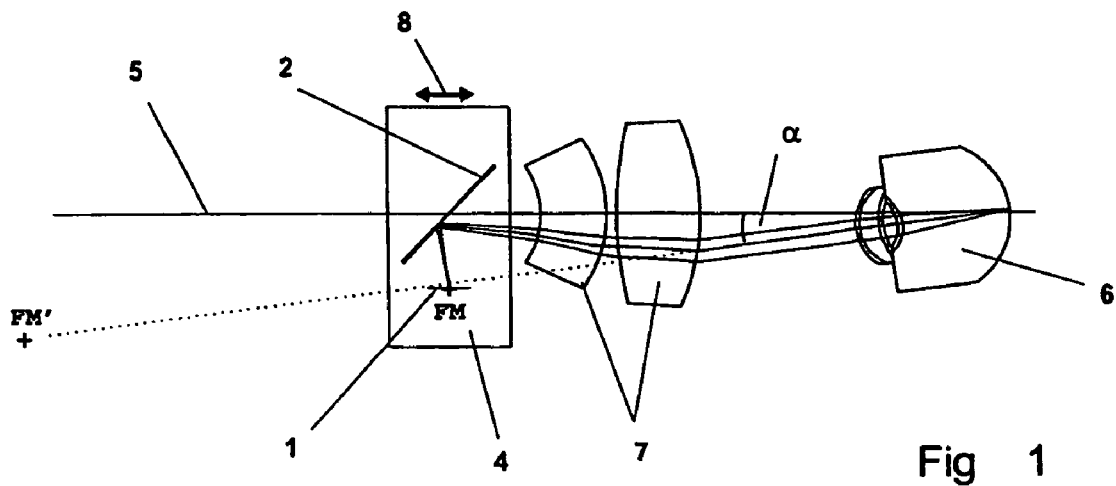
FIG. 1 shows a fixating light source comprising a separate light source with a scanning mirror arranged in front of it.

FIG. 1 shows a fixating light source 4 comprising a separate light source 1 with a scanning mirror 2 arranged in front of it. For the sake of simplicity, a device for coupling the fixating mark FM into a beam path of the ophthalmological apparatus is not shown in the drawing. Instead, the fixating light source 4 is shown only in relation to the optical axis 5 of the ophthalmological apparatus and the eye 6 to be examined and/or treated. The positionable fixating mark FM generated by the fixating light source 4 is projected by the imaging optics 7 of the ophthalmological apparatus in direction of the eye 6 to be examined and/or treated such that the patient sees its image FM' in sharp focus. The control unit provided for generating the fixating mark FM and/or the image FM' thereof at different distances and angular positions with respect to the optical axis 5 is also not shown. Through a corresponding deflection of the scanning mirror 2, the angle α at which the fixating mark FM or its image FM' is visible changes.

In a particular constructional variant of this solution, the separate light source 1 can be arranged in such a way that a scan unit that is already present in the ophthalmological apparatus can be used to generate an image of the fixating mark FM at different distances and angular positions. In particular, the scanning elements existing in the therapy beam paths can be used for this purpose in order to orient the eye for the therapeutic treatment. However, this has the disadvantage that the fixating mark can no longer be used to orient the eye during the therapeutic treatment because a movement takes place simultaneous with the therapy beam.

In a second embodiment form, the fixating light source for generating the positionable fixating mark FM comprises a display or array on which the fixating mark FM can be displayed at any location. The display or array is constructed as a self-luminous or illuminated unit.

Figure 2:
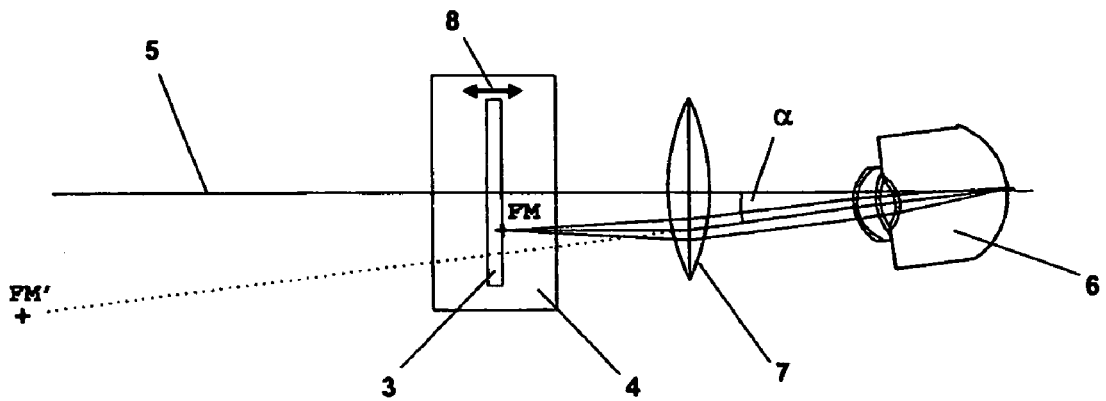
FIG. 2 shows a fixating light source comprising an array.

FIG. 2 shows a fixating light source 4 comprising an array 3. Again, a device for coupling the fixating mark into a beam path of the ophthalmological apparatus is not shown in the drawing and, instead, the fixating light source 4 is shown only in relation to the optical axis 5 of the ophthalmological apparatus and the eye 6 to be examined and/or treated. The positionable fixating mark FM generated by the fixating light source 4 is projected by the imaging optics 7 of the ophthalmological apparatus in direction of the eye 6 to be examined and/or treated so that the patient sees its image FM' in sharp focus. The control unit provided for generating the fixating mark FM and/or the image FM' thereof at different distances and angular positions with respect to the optical axis 5 is also not shown. By controlling different pixels of the array 3 in a corresponding manner, the fixating mark can be displayed at different locations of the array 3 so that the angle α at which the fixating mark FM is visible changes.

In all of the constructional variants mentioned above, there is an optional possibility for taking into account individual requirements for the axial image position in the imaging of the generated, positionable fixating mark FM by the imaging optics 7 of the ophthalmological apparatus. This can be realized by changing the relative position of the generated fixating mark in relation to the imaging optics 7 of the ophthalmological apparatus (shown by arrow 8).

The change in distance causes a change in the image position or in the divergence of the beam bundle between the ophthalmological apparatus and the eye 6. This functionality can be used to solve various tasks such as, for example:

- diopter compensation for patients with defective vision,
- compensation of a change in the refractive index between the ophthalmological apparatus and the eye (e.g., aqueous solution instead of air),
- adapting to a change in the refractive index when using a contact lens or the like.

In a special construction it is conceivable that, based on this functionality (change in divergence/diopter compensation), the patient performs the final focusing of the fixating mark himself or herself by means of a control such as, e.g., a joystick.

Aside from the effects mentioned above, it would also be possible, for example, to change the imaging scale of the system.

In a particularly advantageous construction, the device for coupling in the positionable fixating mark FM is arranged at the co-observation beam path of the ophthalmological apparatus.

Figure 3:
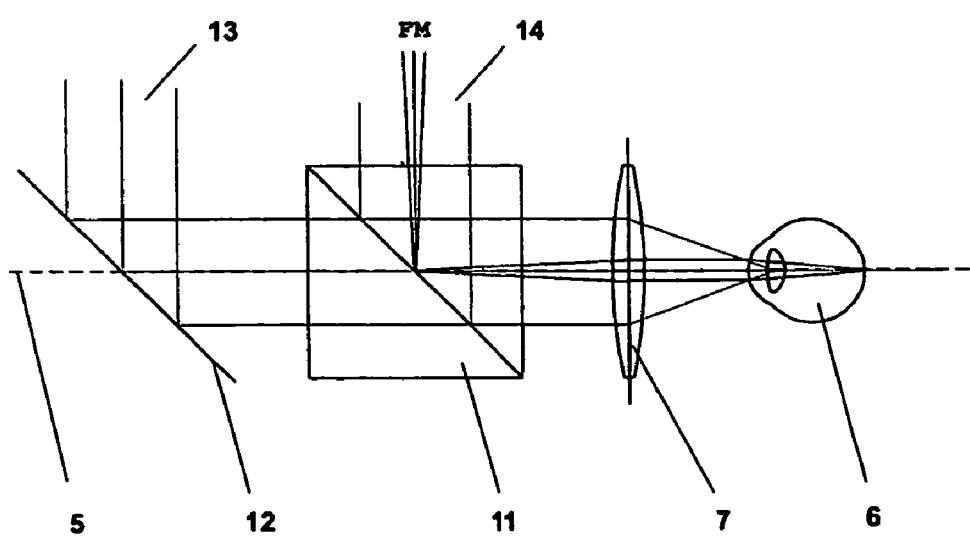
FIG. 3 shows an arrangement for coupling the fixating mark into the co-observation beam path.

FIG. 3 shows an arrangement for coupling the fixating mark into the co-observation beam path of an ophthalmological apparatus.

As was already described, the scanning mirror 12 existing in a therapy beam path 13 can be used with the fixating mark FM to orient the eye 6 for the therapeutic treatment in relation to the optical axis 5. However, the fixating mark FM can no longer be used for orientation during the therapeutic treatment. In order to be able to use it for orientation also during the therapeutic treatment, the coupling in of the positionable fixating mark FM is carried out in the co-observation beam path 14. For this purpose, an additional beamsplitter 11 is arranged in the beam path of the ophthalmological apparatus in front of the imaging optics 7. This makes it possible to use the fixating mark FM for orientation of the eye 6 also during the therapeutic treatment.

The image of the fixating mark FM is manipulated in such way by the control unit that it appears at different distances and angular positions with respect to the optical axis of the ophthalmological apparatus so that the eye to be examined and/or treated is oriented to this fixating mark FM by foveal focusing and occupies a defined position with respect to the optical axis of the ophthalmological apparatus.

While this is carried out by a corresponding deflection of the scanning mirror in the first construction in which the fixating light source comprises a separate light source with a scanning mirror arranged in front of it, the fixating mark is displayed at any locations by a corresponding control in the second embodiment form in which the fixating light source comprises a display or array. The eye to be examined and/or treated orients itself to this fixating mark by foveal focusing and occupies a defined position with respect to the optical axis of the ophthalmological apparatus. The projection device required for this or the location for the display of the image of the fixating mark is calculated beforehand by the control device.

In another embodiment, to manipulate the image of the fixating mark the control unit is connected to a detector unit which monitors the orientation of the eye to be examined and/or treated. In this way it is possible to carry out the adjustment of the desired orientation of the eye iteratively, i.e., the orientation is monitored and, when required, is corrected by approximation (closed control loop).

In a method according to the invention for the orientation of an eye for diagnostic and/or therapeutic purposes, the positionable fixating mark generated by a fixating light source is coupled into the beam path of the ophthalmological apparatus and is projected by its imaging optics in direction of the eye to be examined and/or treated, wherein an image of the fixating mark can be displayed at different distances and angular positions with respect to the optical axis of the ophthalmological apparatus, the eye to be examined and/or treated is oriented to this fixating mark through foveal focusing and occupies a defined position with respect to the optical axis of the ophthalmological apparatus.

As was already described, the positionable fixating mark can be generated by a fixating light source in the form of a separate light source preceded by a scanning mirror. A self-luminous object or the image thereof or an illuminated diaphragm or the image thereof is used as separate light source. Or the positionable fixating mark is generated by a display or array in that the fixating mark can be displayed at any locations, wherein a self-luminous or illuminated unit is used as display or array.

In an advantageous embodiment, the coupling in of the positionable fixating mark is carried out in the co-observation beam path of the ophthalmological apparatus. This was also already described.

In order that the eye to be examined and/or treated is oriented on this fixating mark by foveal focusing and to bring it into a defined position with respect to the optical axis of the ophthalmological apparatus, an image of the fixating mark is generated by an existing control unit at different distances and angular positions with respect to the optical axis of the ophthalmological apparatus.

The required location of the display of the image of the fixating mark is calculated by the control unit for this purpose.

In another embodiment, the control unit is connected to the detector unit monitoring the orientation of the eye in order to achieve the desired orientation iteratively. The fixating mark need not be visible for the detector unit.

The position of a characteristic point in relation to a target coordinate is determined by means of the detector unit. By characteristic point is meant such points as are suitable through determined optical features to be distinguished from their surroundings. For example, the pupil center is used for this purpose. Existing observation units and/or imaging units of the ophthalmological devices can be used as detector unit. The use of a camera unit which photographs the eye to be examined and/or treated, including the characteristic point, is particularly advantageous in this regard. The electronic image of the eye, including the image of the fixating mark and the target coordinate which can correspond, for example, to the optical axis 5 of the ophthalmological apparatus, are starting quantities for the evaluation of the position and the determination of the correction coordinates.

If the positional deviation ($\Delta x$; $\Delta y$) is determined (manually or automatically), control signals are derived therefrom and are supplied to the fixating light source, and the position of the fixating mark or its image is corrected. The patient's eye follows this movement and accordingly changes its position relative to the ophthalmological apparatus. After the movement of the patient's eye, its position relative to the target coordinate can be monitored again and, if need be, corrected. A closed control loop is arranged in this way.

Figure 4:
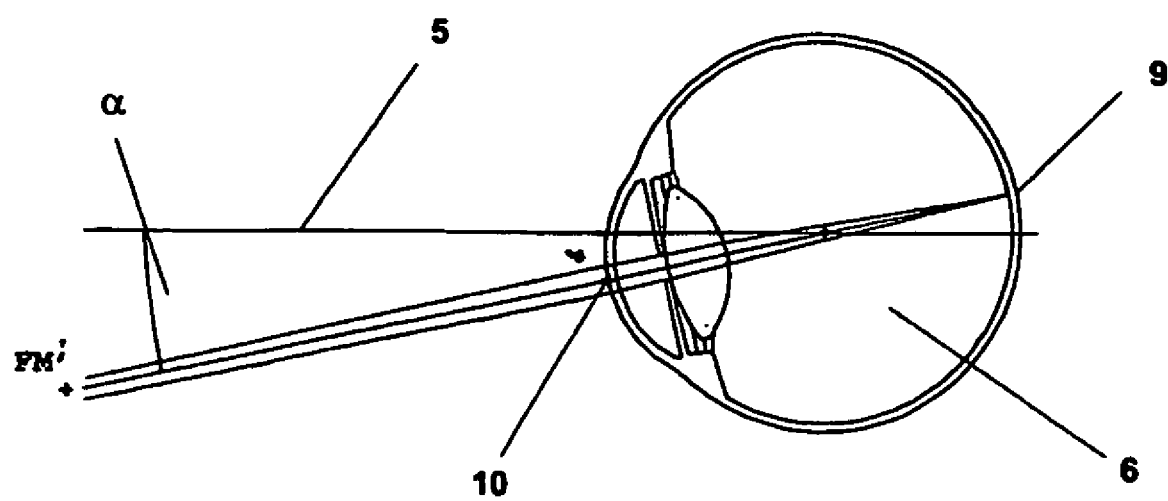
FIG. 4 shows an eye to be examined and/or treated.

For a more detailed description, FIG. 4 shows an eye 6 to be examined and/or treated with the beam path of the fixating mark FM.

In order to use the ophthalmological apparatus (diagnostically or therapeutically), the eye 6 must be oriented with respect to the optical axis 5 of the ophthalmological apparatus.

A visible fixating mark FM is presented by the fixating light source 4 to the eye 6 at different angles a to the optical axis 5 to which the eye 6 orients itself by foveal focusing in that the eye 6 moves in the eye socket such that the fixating mark FM is sharply imaged in the macula 9.

The position of a characteristic point, e.g., the pupil center 10, is determined in relation to a target coordinate ZK by means of the detector unit. In an iterative approximation, the target coordinate ZK initially lies on the optical axis 5. The visible fixating mark FM is now presented at an angle a to the optical axis 5.

If the image acquisition and image evaluation are computer-supported, the orientation of the eye to be examined and/or treated and its position at a defined location with respect to the optical axis of the ophthalmological apparatus is carried out automatically.

The solution according to the invention enables the orientation of an eye for diagnostic and/or therapeutic purposes in a simple manner.

Most of the solutions known from the prior art implicitly assume that the position and orientation of the patient's eye must always be optimized as substantially independent parameters to enable correct image generation in diagnostic methods or a correct treatment in therapeutic methods. While this is often the case for applications in the posterior portion of the eye, it is usually not the case in the anterior portion of the eye. In particular, in observation or treatment of the cornea, usually only the exact position of the cornea in space is decisive.

In contrast to the known solutions, the proposed technical solution assumes that the rotating movement of the eye in the eye socket that is carried out during a change in the line of sight is also used to change the position of the cornea.

For this purpose, a positionable fixating mark is moved in a defined manner and is projected in direction of the eye to be examined and/or treated, which eye is oriented on this fixating mark by foveal focusing and occupies a defined position with respect to the optical axis of the ophthalmological apparatus.

In the proposed solution, it is particularly advantageous that the eye to be examined and/or treated can be oriented in direction of the optical axis of the ophthalmological apparatus as well as in any other direction.

The invention claimed is:

1. A device for the orientation of an eye for diagnostic and/or therapeutic purposes comprising:
   a fixating light source for generating a positionable fixating mark;
   a device for coupling this fixating mark into a beam path of an ophthalmological apparatus whose imaging optics project the fixating mark in direction of the eye to be examined and/or treated; and
   a control unit by which the image of the fixating mark can be displayed at different distances and angular positions with respect to the optical axis of the ophthalmological apparatus so that the eye to be examined and/or treated is oriented to this fixating mark by foveal focusing and occupies a defined position with respect to the optical axis of the ophthalmological apparatus.

2. The device according to claim 1;
   wherein the fixating light source for generating the positionable fixating mark comprises a separate light source with at least one scanning mirror arranged in front of it.

3. Devices according to claim 2;
   wherein a self-luminous object or its image or an illuminated diaphragm or its image is used as separate light source.

4. Devices according to claim 1;
   wherein the fixating light source for generating the positionable fixating mark comprises a display or array on which the fixating mark can be displayed at any locations.

5. Devices according to claim 4;
   wherein the display or array is constructed as a self-luminous or illuminated unit.

6. Devices according to claim 1;
   wherein the device for coupling in the positionable fixating mark is arranged at the co-observation beam path of the ophthalmological apparatus.

7. Devices according to claim 1;
   wherein the control unit is connected to a detector unit which monitors the orientation of the eye to be examined and/or treated.

8. Devices according to claim 1;
   wherein the fixating light source is constructed in such a way that the distance of the generated fixating mark from the imaging optics can be changed in order to display the image of the fixating mark in different focusing planes along the optical axis.

* * * * *

UNITED STATES PATENT AND TRADEMARK OFFICE
CERTIFICATE OF CORRECTION

PATENT NO. : 8,262,223 B2  
APPLICATION NO. : 12/224960  
DATED : September 11, 2012  
INVENTOR(S) : Mark Bischoff et al.

Page 1 of 1

It is certified that error appears in the above-identified patent and that said Letters Patent is hereby corrected as shown below:

Title Page

<u>Item 75 Inventor Address</u>:

Inventor Dr. Mark BISCHOFF's address should read as follows:

--Im Kraehmer 12
07749 Jena
Germany--

Signed and Sealed this
Twenty-third Day of April, 2013

Teresa Stanek Rea
*Acting Director of the United States Patent and Trademark Office*